(12) United States Patent
Chan et al.

(10) Patent No.: US 9,008,784 B2
(45) Date of Patent: Apr. 14, 2015

(54) DEVICE AND METHODS FOR PREVENTING KNEE SPRAIN INJURIES

(71) Applicant: The Chinese University of Hong Kong, Shatin (CN)

(72) Inventors: Kai-Ming Chan, Shatin (CN); Tik-Pui Daniel Fong, Shatin (CN); Shu-Hang Patrick Yung, Shatin (CN)

(73) Assignee: The Chinese University of Hong Kong (CN)

( * ) Notice: Subject to any disclaimer, the term of this patent is extended or adjusted under 35 U.S.C. 154(b) by 0 days.

(21) Appl. No.: 13/830,635

(22) Filed: Mar. 14, 2013

(65) Prior Publication Data

US 2014/0277271 A1 Sep. 18, 2014

(51) Int. Cl.
*A61N 1/00* (2006.01)
*A61N 1/36* (2006.01)

(52) U.S. Cl.
CPC ........ *A61N 1/36003* (2013.01); *A61N 1/36014* (2013.01)

(58) Field of Classification Search
CPC ........... A61N 1/36003; A61N 1/36128; A61N 1/36132

USPC ...................................................... 607/48–52
See application file for complete search history.

(56) References Cited

U.S. PATENT DOCUMENTS

2010/0042182 A1* 2/2010 Chan et al. ...................... 607/48

* cited by examiner

*Primary Examiner* — Allen Porter, Jr.
(74) *Attorney, Agent, or Firm* — Kilpatrick Townsend & Stockton, LLP; Kenneth R. Shurtz, Esq.

(57) ABSTRACT

Devices and methods for preventing knee sprain injuries. To protect the knee joint from knee sprain injuries, the device comprises a sensing part configured to sense data associated with knee motion; an analyzing part configured to analyze the knee motion data to determine a knee articulation; and a stimulating part configured to stimulate one or more lower limb muscles to initiate an earlier muscle reaction than would naturally occur in response to the determined knee joint articulation. The determined knee joint articulation may include knee joint articulation or a particular type of articulation such as a knee sprain movement associated with knee sprain. The methods involve sensing data associated with knee joint motion, analyzing the data to determine a knee joint articulation; and stimulating one or more lower limb muscles to initiate an early muscle reaction within the determined knee joint articulation.

27 Claims, 9 Drawing Sheets

DEVICE AND METHODS FOR PREVENTING KNEE SPRAIN INJURIES

BACKGROUND

The present invention relates to devices and methods for preventing knee sprain injuries by improving joint articulations through myoelectric stimulation. In particular, the invention provides a device for improving muscle coordination to prevent joint articulation of the knee that may result in knee sprain injuries.

DESCRIPTION OF THE RELATED ART

Injuries to muscles, ligaments and bones in lower limbs, such as the anterior cruciate ligaments (ACL), are fairly common in sports, which may cause pain and immobility of the legs or knee joints. For example, knee sprain injuries may result in tearing or rupture of the ACL and meniscus, often requiring surgery to reconstruct the damage structures. Often the damage cannot be fully repaired rehabilitated through conventional treatments and may lead to life-long pain and limited joint movement and instability, which in turn may lead to repeated knee joint injuries.

Studies have suggested that most knee sprain injuries are typically caused by excessive knee valgus and tibial internal rotation mechanism. Conventional treatments include exercise to develop and strengthen the muscles affecting knee valgus and tibial internal rotations, as well as braces and application of athletic tape that attempt to avoid knee articulation that may result in repeated injury to the joint. While these treatments may provide some relief for some patients, often such treatments have mixed results. In addition, physical therapy can be a fairly gradual and time-consuming course of treatment, while application of athletic tape and braces may cause discomfort and unnecessarily limit range of motion and interfere with athletic performance, as well as routine daily activities. Therefore, there exists a need methods and devices that improve articulation of the knee joint to inhibit knee sprain injuries as well as prevent repeated joint sprains after such an injury has occurred that provides improved more consistent articulation of the knee joint. In addition, it is desirable for such treatments to allow patients to maintain a natural range of movement in the knee joint while improving patient comfort and adherence to treatment.

BRIEF SUMMARY

The present invention relates to prevention of knee joint sprains or injuries by use of myoelectric stimulation. In one aspect, the invention stimulates muscles affecting knee joint movement to initiate muscle function of select hip and thigh muscles to improve knee joint articulation and prevent knee joint sprain injuries. In particular, the invention seeks to prevent knee joint sprain injury by sensing a knee joint articulation and initiate a muscle reaction in the muscles before the patient's natural muscle reaction by use of an artificial trigger, such as an electrical stimulation, delivered to the muscle. In some embodiments, the sensed knee joint articulation is a particular type of articulation or joint movement exceeding a threshold associated with knee joint sprain injuries, such a valgus or internal rotation displacement or velocity, and the stimulation is configured to stimulate select hip and thigh muscles to reduce the valgus displacement or internal rotation to prevent the knee joint sprain movement.

According to one aspect of the invention, a device for preventing a knee sprain injury includes a sensing part, an analyzing part and a stimulation part. The sensing part is configured for sensing knee joint movement and the analyzing part configured to determine whether the sensed knee joint movement corresponds to a knee joint articulation, in particular a knee sprain movement associated with knee sprain injuries. The stimulating part is configured to stimulate one or more muscles associated with knee movement in response to the determination by the analyzing part so as to improve the knee joint movement and prevent knee joint sprain injury.

In certain embodiments of the invention, the sensing part may include a motion sensor, such as one or more accelerometers or other such sensors, that may detect movement of the knee and/or an angular deflection or alignment of the knee joint, and may further sense data relating to any or all of knee valgus or internal rotation displacement or velocity. The sensing part may be positioned at or near the knee joint, or may include one or more sensors positioned at various other locations on the body, for example the thigh, calf, foot, or waist regions that may be used to improve sensing of knee movement and alignment indicative of a knee joint articulation, and in particular a knee joint sprain movement. The sensing part may include one or more sensors at or above the knee and one or more sensors at or below the knee such that comparison of sensed data between each set of one or more sensors can be used to determine a particular knee joint articulation, such as a knee joint sprain movement. In certain aspects, one or both sets of the one or more sensors may include a batch of sensors that extend at least partially circumferentially around a thigh or shank of a user when the device is worn by the user. The one or more sensors below the knee may further include a foot motion sensor adapted to measure a state of the foot.

In certain embodiments, the stimulating part includes one or more electrode pair configured to apply myoelectrical stimulation to the muscles on which the electrodes are applied. The electrodes may include one or more patches to be adhered to the surface of the skin over a muscle, such as the hip and thigh muscles, in particular a muscle of the hip abductor/adductor group and the knee internal/external rotator group, such as the gluteus medius and the biceps femoris. In any of the embodiments described herein, the stimulation part and sensing part, as well as other components of the device, may be incorporated into a wearable device, such as a brace or athletic garment to be worn by a user to prevent injury during athletic activity.

According to another aspect of the present invention, a method for preventing a knee sprain injury is provided, which comprises sensing data of a knee joint articulation; analyzing the data to judge whether the motion is a sprain motion; and stimulating one or more lower limb muscles to inhibit or correct the motion if the determined motion is a sprain motion.

DETAILED DESCRIPTION

Embodiments of the present invention relate to prevention of knee sprain injuries by use of an artificial trigger to stimulate muscle function. Although embodiments make specific reference to myoelectric muscle stimulation delivered with adherent electrode patches, the systems and methods described herein may be used in any application in which muscle stimulation is triggered to alter or maintain a knee joint articulation to prevent knee sprain injuries.

Knee joint injuries are common-place among athletes in many sports. Knee joint sprain, in particular, is often the mechanism that leads to anterior cruciate ligament and meniscus tear, usually requiring operative treatment to reconstruct the damaged structures. In the long term, such injuries may lead to knee joint instability and early development of osteoarthritis. By use of the features described herein, the device operates to protect the knee joint from sustaining ligamentous rupture in an acute knee valgus sprain injury.

Currently, myoelectric stimulation has been employed in various medical devices, such as "Functional Electric Stimulus" (FES), to initiate passive exercise to injured muscles for rehabilitation training. Moreover, similar technologies are employed in passive massage devices. In addition, similar techniques have been employed to assist walking in hemiplegic patients who cannot deliver neuromuscular activation to the leg muscle to walk. In all of these devices, electrical signals are delivered to the selected muscle group through pairs of electrodes, which replace the human intrinsic neuromuscular electrical stimulation. The electrical signals can trigger some biochemical changes in muscle cells, leading to contraction of the muscle and thus joint flexion or extension. However, these devices cannot provide quick reaction to prevent acute knee sprain injuries.

The injury mechanism in a typical knee sprain injury is believed to be excessive knee valgus motion, with the presence of excessive internal rotation. One etiology of the injury is the slow reaction time of some thigh and hip muscles, which functions to abduct the hip and externally rotate the knee. The muscles reaction time is about 60-90 ms, which is a bit later than the time for an injury to occur (50 ms). Therefore, in most of the injuries, due to this delay, the muscles are unable to "catch up" after onset of the injurious sprain movement and are unable to protect the knee joint before knee sprain injury occurs.

In one aspect, the present invention seeks to alter the natural muscle reaction by myoelectric stimulation to improve the reaction time and coordination of the muscles affecting knee joint movement so as to inhibit the knee sprain movement before knee joint sprain occurs, thereby preventing knee sprain.

Figure 1:
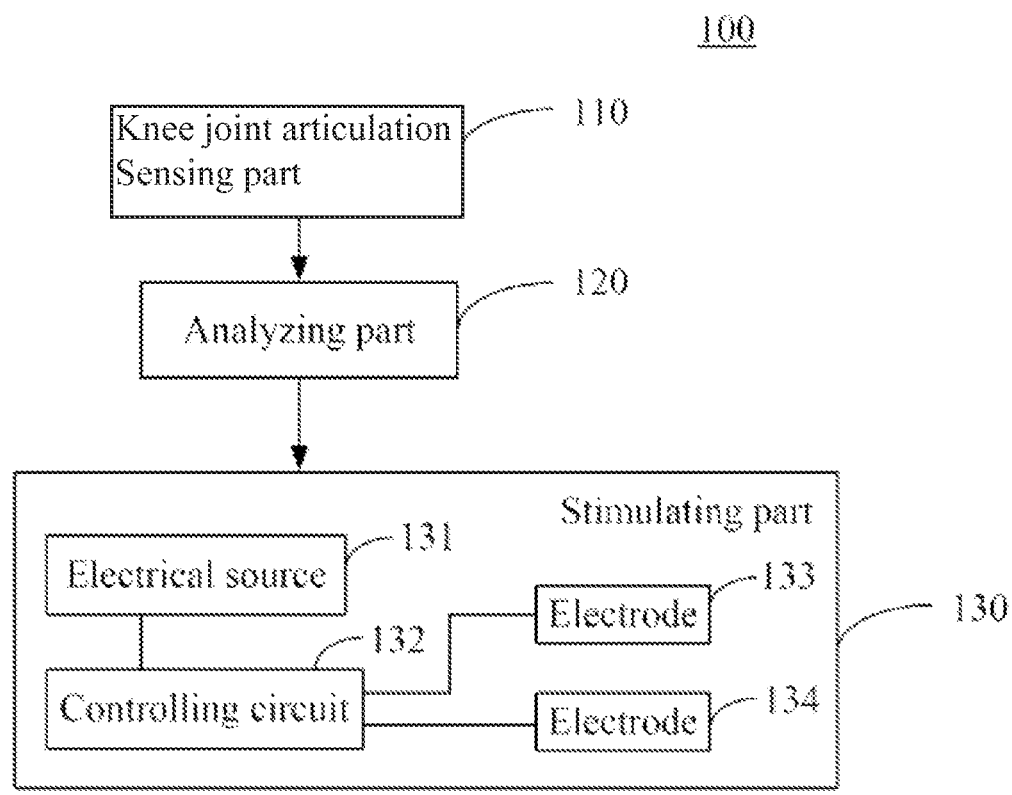
FIG. 1 shows a schematic block diagram of the device for preventing a knee sprain injury according to an embodiment of the present invention.

In the example of FIG. 1, the device 100 includes a sensing part 110 for sensing data associated with movement of the knee joint, an analyzing part 120 configured to analyze the received sensing data and a stimulation part 130 configured to deliver a stimulation energy to one or more muscles of the lower body that affect movement of the knee joint in a manner to prevent knee sprain injury.

The sensing part 110 may include any sensor adapted to detect data relating to movement data of the knee joint. The detected movement may be associated with any articulation or bending of the knee joint, or with a particular knee joint movement such as bending of the knee with knee valgus displacement or internal rotation often associated with knee sprain injuries. In certain aspects, the sensor 110 includes one or more sensors above the knee and one or more sensors below the knee such that a determination of a particular knee joint movement can be made by a processor of the analyzing part 120 using measurements from the set of one or more sensors above and below the knee. The one or more sensors may comprise any of the sensors described herein or any sensor suitable for detecting data relating to position or movement of the user. For example, a particular knee joint movement can be determined by comparing a state measurement of a sensor above the knee to a state measurement of a sensor below the knee (e.g. a relative, position, velocity and/or acceleration). The one or more sensors below the knee may be positioned at any of various locations from a position adjacent the knee to the foot, while the one or more sensors above the knee may be positioned at any of various locations from adjacent the knee to the thigh or even a mid-section or upper body portion of the user. In certain aspects, the one or more sensors above the knee are positioned on the user so as to detect or track a state of the femur, while the one or more sensors below the knee are positioned on the user so as to detect or track a state of the tibia. The state of each of the femur and tibia may include a position, velocity, acceleration or any combination thereof. In certain embodiments, one or both sets of the one or more sensors may include a batch or array of sensor that extend circumferentially, either partially or entirely, around the thigh or shank of the patient when the device is worn by the user. In such embodiments, the motion of the batch of sensors may be filtered to remove movement or displacement associated with movement of the skin of the user. The one or more sensors below the knee may also include a foot motion sensor that can be used to detect or track a state of a foot of the user. The foot motion sensor may include a pressure sensor on either or both the heel and the fifth metatarsal head so as to detection of an impact associated with landing a jump and/or may include an accelerometer or other sensor to provide tracking of an alignment of the foot relative to the body, which may be particularly useful in detecting the knee-in toe-out mechanism often associated with a knee joint sprain movement.

The sensed motion data may also include a combination of data relating to various movements or positions of the user's anatomy that, in combination, can be used to determine the knee joint articulation and whether the articulation is a sprain motion. For example, a sensing part may utilize a sensor on the foot to determine a foot alignment relative to the knee joint to determine whether the knee joint articulation is associated with a knee-in to-out mechanism, often associated with knee joint sprain injuries.

The analyzing part may include a processor having a readable memory with a program recorded thereon for determining whether the sensed movement data is indicative of knee joint articulation, and in particular whether the knee joint articulation corresponds to a knee joint sprain movement. In many embodiments, the analyzing part includes a pre-defined threshold value relating to the sensed knee joint motion data that are indicative of a sprain motion. In some embodiments, the threshold may be adjustable or may vary according to the requirements or characteristics of the user or according to the application, such as the sport or activity in which the user partakes during operation of the device. Often, the analyzing part is included on the device and wired directly to the sensing part and the stimulation part, although it is appreciated that the analyzing part may be connected wirelessly and be separate from the device worn by the user.

The stimulating part 130 may include one or more electrodes pairs 133, 134 adapted to deliver sufficient electrical energy to stimulate the muscle (e.g. stimulation sufficient to contract or initiating early contraction of the muscle). Each electrode pair may be provided on adherent patch applied to a skin surface of the user. The stimulating part 130 may include an electrical power source 131, one or more electrode pairs 133, 134, and a controlling circuit 132. In many embodiments, the stimulating part is adapted for myoelectric stimulation, the controller coupling the power source to the electrode being configured to deliver a myoelectric stimulation to one or more muscles through the electrode.

In some embodiments, the device includes a battery for power supply, a circuit board to raise the output voltage to the desired level, and one or more pairs of electrodes adapted for attachment to a skin surface of the user on the select muscles. The device may include a circuit to trigger auto-off after a period of time, say, 0.5 second after the occurrence of potential spraining risk.

Figure 2:
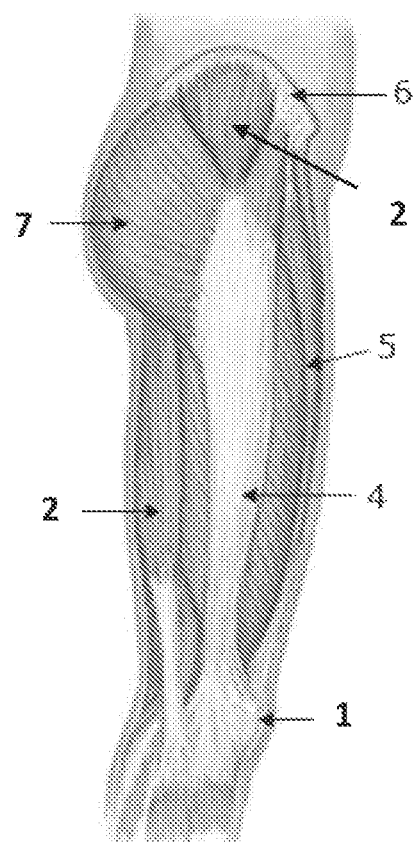
FIG. 2 is a diagram of the anatomy of an upper leg that determines articulation of the knee joint.

FIG. 2 illustrates the anatomy of the lower body which relates to articulation or movement of the knee joint and to which the device is applied. Articulation of the knee joint 1 relies on a complex interaction between various muscles and ligaments in a coordinated manner to provide a properly aligned articulation for avoiding knee injuries. Among the thigh and hip muscles affecting and controlling knee joint articulation are the biceps femoris 2, the gluteus medius 3 (connected to the iliac crest 6 and adjacent the gluteus maximum 7), the iliotibial band 4 and vastus lateralis 5. In particular, the biceps femoris 2 and the gluteus medius 3 control the knee valgus displacement and internal rotation, such that muscle reaction of one or both of these muscles allows the device to significantly improve the knee joint articulation and inhibit knee joint sprain movement to prevent knee joint sprain injuries.

For example, in a case where the knee-in toe-out mechanism is present, stimulating the gluteus medius may abduct the hip joint to change the "knee-in" or valgus orientation back to a neutral straight alignment. In addition, excessive internal rotation, which is often considered a common cause of ACL rupture, may be corrected by stimulating the knee joint internal rotator muscle. In many embodiments, the device detects such cases where a knee-sprain mechanism may be present and stimulates one or more such muscles thereby allowing an earlier muscle reaction than would naturally occur to allow the mechanism to be corrected by the stimulated muscles, thereby preventing the knee sprain.

Figure 3A:
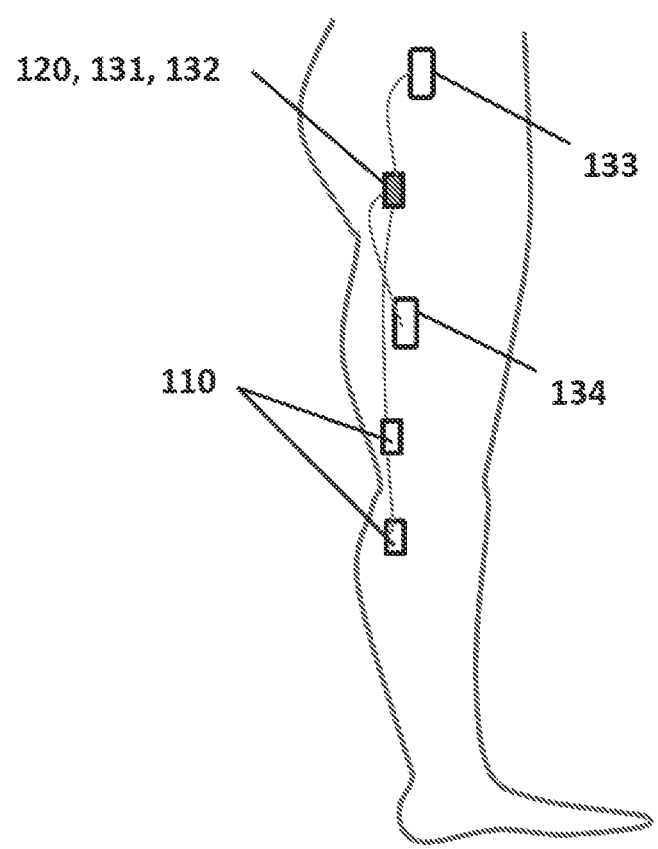
FIGS. 3A-3C illustrate a device in accordance with embodiments of the invention as worn by a user.
Figure 3B:
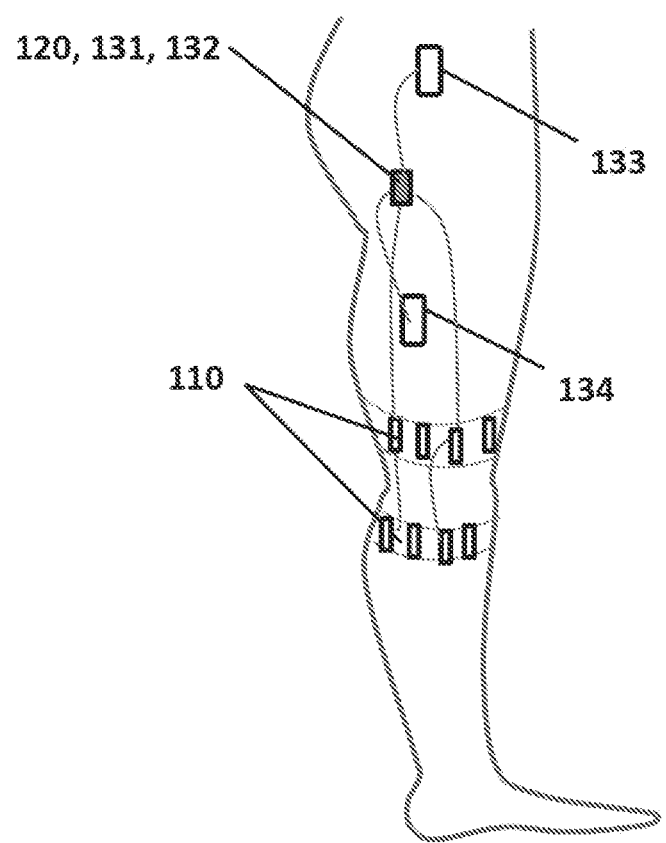
Figure 3C:
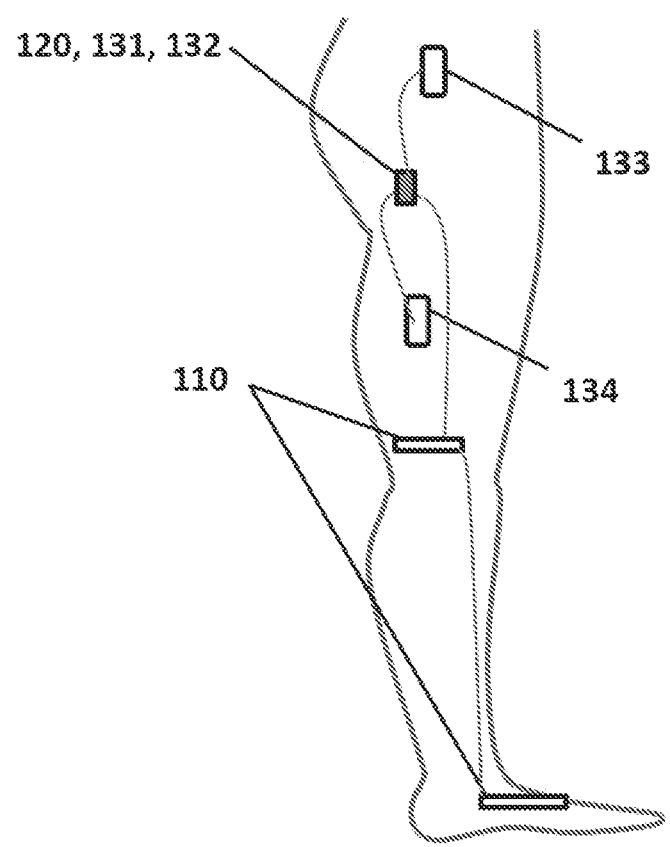

FIGS. 3A-3C show the anatomy of the lower body and example devices applied thereto. In each of the examples of FIGS. 3A-3C, the device includes an electrical power source 131 and controlling circuit 132, sensing part 110, analyzing part 120, and stimulating electrodes 133 and 134. It is appreciated that the electrical power source 131, controlling circuit 132 and analyzing part 120 may be incorporated into a single unit worn by the user or may be included as separate components. In FIG. 3A, the device includes a stimulating pair on each of the thigh and hip muscles, although it is appreciated that the device may be used with a stimulating electrode pair only on select hip muscles or only on select thigh muscles. The sensing part 110 includes a sensor, such as an accelerometer or other suitable sensor, above the knee and another such sensor below the knee. FIG. 3B illustrates an alternative embodiment in which the one or more sensors above and below the knee each include a batch of sensors, the batch of sensors extending circumferentially about the thigh and the shank of the user, respectively, so as to track a state of the respective body parts from which the analyzing part 120 can determine a knee joint movement based on a relative state of the thigh and shank. In such embodiments, the movement of the batch of sensors may be filtered or averaged to remove movement associated with movement of the user's skin. FIG. 3C depicts an embodiment having a sensor part 110 with a set of one or more sensors above the knee and another set below the knee, in which the set includes a foot motion sensor. The foot motion sensor include a pressure sensor adapted to detect an impact above a set threshold so as to indicate a foot-strike associated with a landing movement and/or may include an accelerometer or other such sensor to determine an alignment of the foot relative to the body so as to allow a determination by comparison of a body joint position associated with a knee sprain movement, such as a toe-in knee out mechanism. Such a mechanism may also be detected by measuring a distance between sensors on the feet (such as a sensor near the toes of each foot) and measuring a distance between sensors on or adjacent the knees. It is appreciated that the different aspects of these configurations disclosed herein may be combined or used in varying combinations in accordance with the principles and scope of the present invention.

In some embodiments, stimulation of the select hip and thigh muscles is delivered by electrode pairs 133 and 134, respectively, upon determination that a foot strike of a landing task occurred based on impact data sensed at the foot by sensing part 110. This may significantly reduce the knee valgus torque during the landing task. The sensing part may include additional sensor to determine whether a valgus or internal rotation displacement or velocity, such as approximately 30 and 1000 degrees per second.

In certain aspects, the device is configured to deliver an artificial trigger to initiate muscle function before the normal muscle reaction (e.g. an early muscle reaction) by use of the electrode pairs attached to the thigh and hip on the skin surface. Electrical signals are delivered to the muscles through the electrodes when in need, which may be about 20-30 ms after the start of the injurious motion as determined by the analyzing part based on the sensed data from the sensing part. Research indicates that the torque latency of the hip and thigh muscles is about 21-25 ms. Therefore, the device allows the muscles to "catch up" to initiate muscle contraction in order to correct the injurious sprain movement and protect the knee joint.

Figure 4:
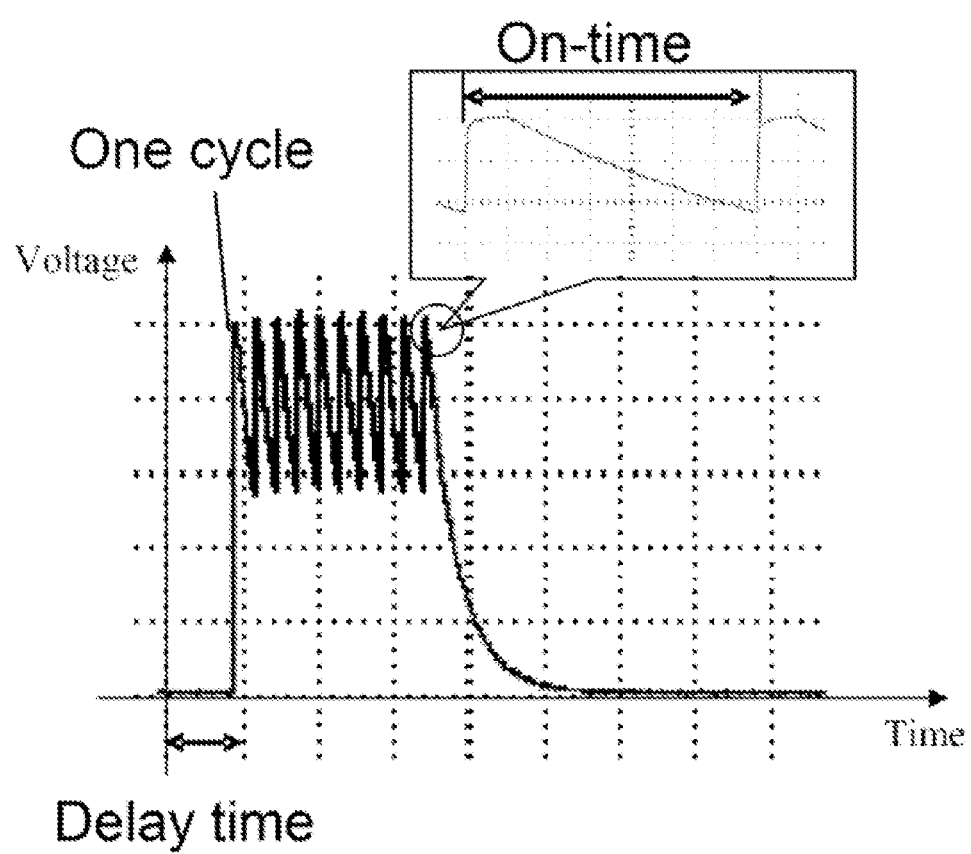
FIG. 4 shows a graph of an example electrical pulse generated by the controlling circuit in accordance with embodiments of the invention.

According to some embodiments, electrode pairs 133 and 134 are attached to the skin surface of the select thigh and hip muscles on the leg of the user and are configure for myoelectric stimulation of the muscles. The electric stimulation signal generated by the controlling circuit 132 is an electrical pulse. An example electrical pulse in accordance with certain embodiments is shown in FIG. 4, the electrical pulse having a plurality of cycles. The on-time (i.e. the width) of one cycle, the number of the cycles and the delay-time from the start of a sprain injury to the start of the electrical pulse may be adjustable as needed for a particular patient or application.

Figure 5:
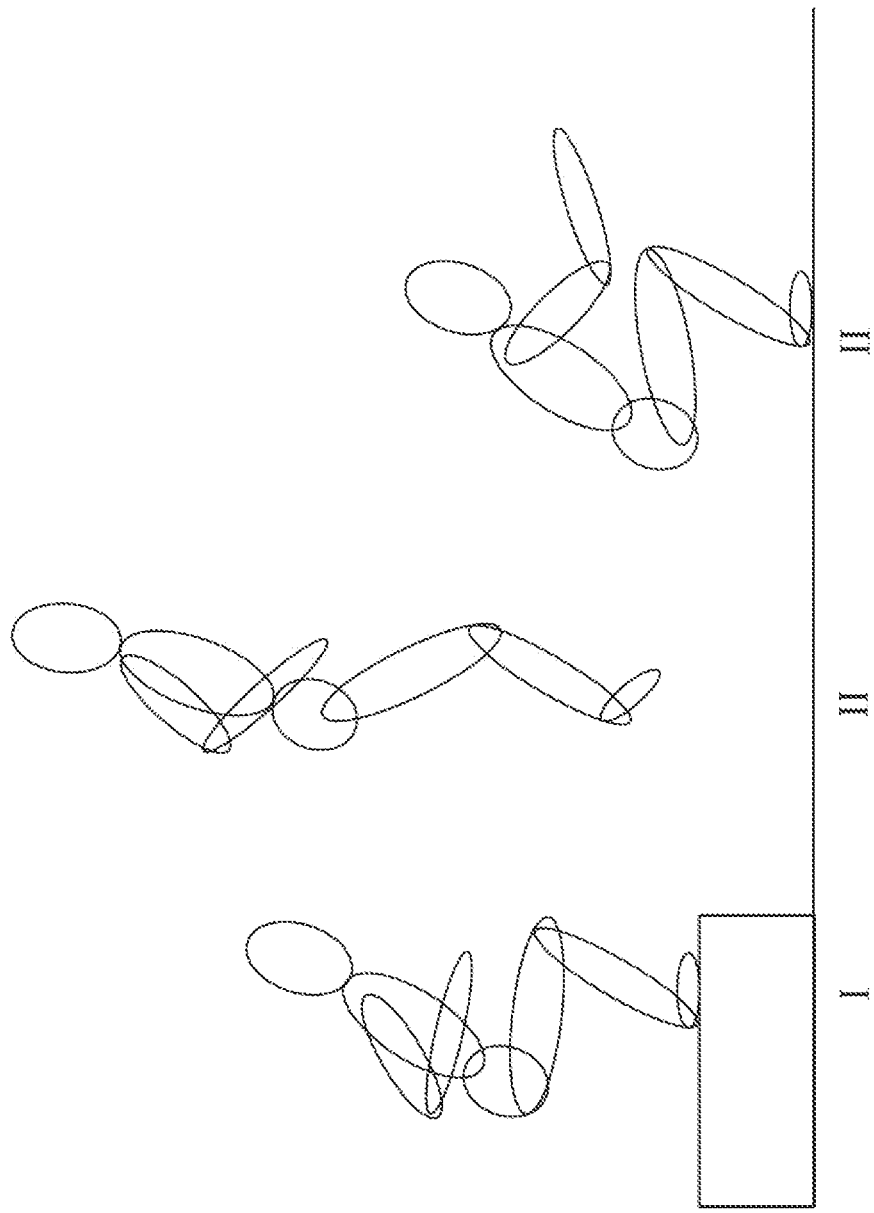
FIG. 5 illustrates a side view of knee joint positions during a forward drop landing task.
Figure 6:
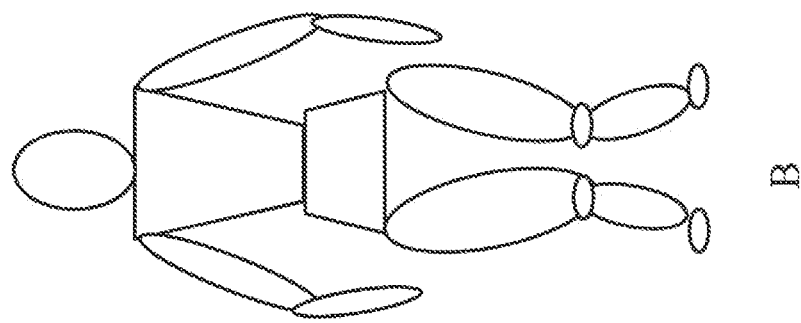
FIG. 6 illustrates front views of two possible landing positions in a forward drop landing task.
Figure 6:
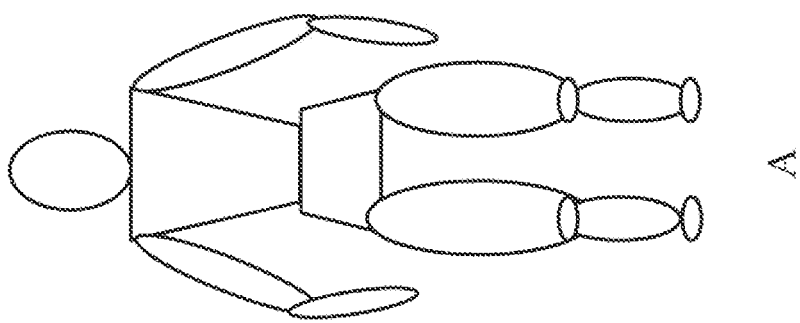
Figure 7:
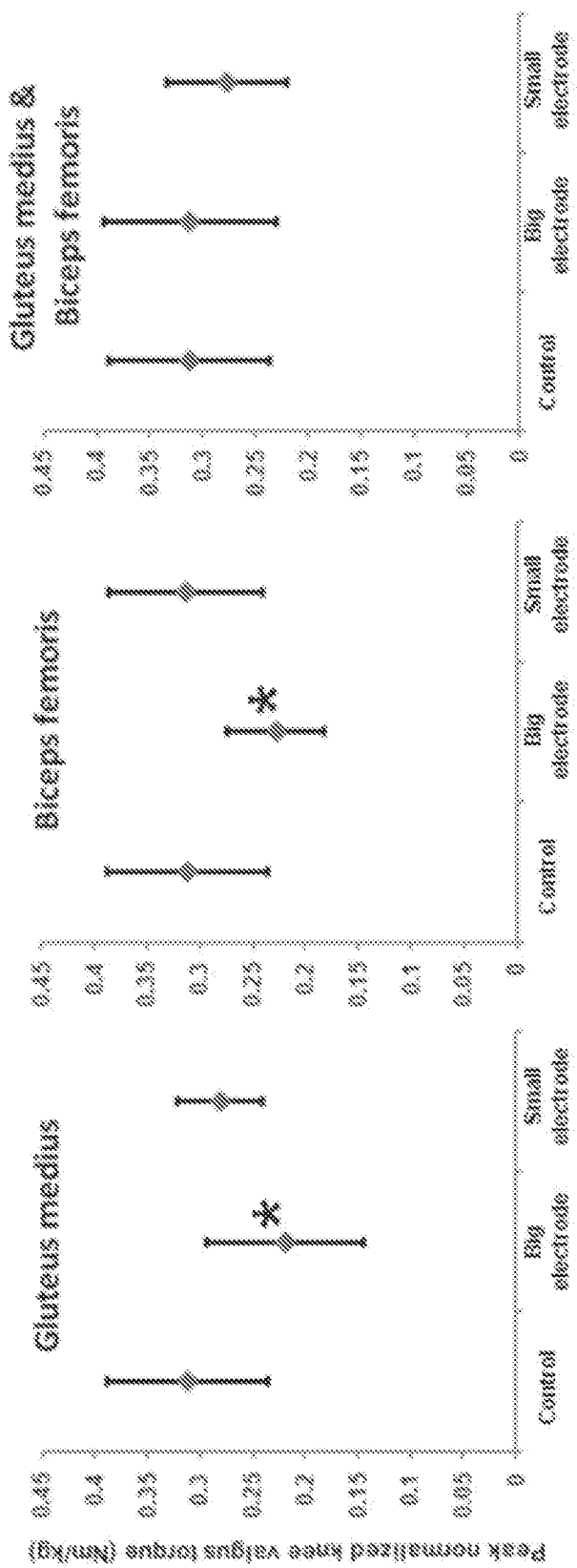
FIG. 7 graphically depicts field test results illustrating the effect of an example device on muscle function in select thigh and hip muscles.

The advantageous effects provided by use of example device in accordance with the present invention in testing trials are set forth in FIG. 7. Twelve female subjects performed a series of drop landing tasks wearing the device. A drop landing task, illustrated in FIG. 5, is one such activity in which a knee sprain movement and injury commonly occurs. As shown in FIG. 5, a user standing on an elevated platform (I), jumps forwards and upwards (II) and then lands in a forward leaning position with knees bend (III). This landing position applies significant stress and force on the knee joint and if not properly aligned can result in a knee sprain movement and subsequent knee sprain injury. FIG. 6 illustrates two possible knee joint positions when landing in a forward drop task. When properly aligned (knees and toes pointed forwards), such as shown in position A, knee sprain is unlikely. However, when mis-aligned (e.g. knees-in toe-out), such as shown in position B, excessive knee valgus or internal rotation directs the forces and stresses in the knee joint in such a way that a knee joint sprain is considerably more likely. In some embodiments, the device is able to determine the misalignment based on the sensed knee joint movement data from the sensing part and applies stimulation to select hip and thigh muscles such that the mis-aligned movement can be corrected by the muscle reaction before knee joint sprain occurs.

FIG. 7 graphically depicts field test results of the device illustrating the effect of the device on muscle function in select thigh and hip muscles. Twelve female subjects performed a forward drop landing task from a height of 40 cm in a biomechanics laboratory. A battery-powered device was used to deliver a 130 V myoelectric stimulation for 500 ms through electrodes of different sizes (38 or 19 square centimeters) to either or both the gluteus medius and biceps femoris when each subject landed. A motion analysis system and a force plate were used to collect the biomechanics data, and the normalized knee valgus torque data was obtained. two-way analysis of variance with repeated measured and post-doc Tukey pairwise comparisons was conducted to demonstrate any significant difference among the tested conditions. Statistic significant was set at a 95% level of confidence. The results indicated a significant interactive effect for each different condition of muscle stimulation. A significant drop was found in stimulating either the gluteus medius or the biceps femoris with the electrode having a larger surface area (30 square centimeters) when compared to the control condition. The results of the study indicated that myoelectric stimulation on either gluteus medius or biceps femoris could reduce the knee valgus torque from 16 to 11 Nm during a forward drop landing task.

In operation, the sensing part 110 senses and transmits the data associated with knee joint articulation in a real-time manner. In an implementation, the sensing part 110 comprises a tri-axial accelerometer and a gyrometer for sensing motions of the foot segment relative to the shank segment. In this case, the data to be sensed and transmitted is the velocity of the user's knee during articulation. The knee valgus velocity refers to the velocity at which knee valgus displacement occurs, and in turn, internal rotation velocity refers to the velocity at which internal rotation occurs. Such movement may be sensed directly or indirectly through sensing of foot movement or position relative the body.

The sensing part 110 may comprise one or more selected from the group consisting of a tri-axial accelerometer, a gyrometer, a goniometer, a pressure sensor and the like. In certain embodiments, the sensing part 110 comprises a pressure sensor to sense the motions of the foot segment, such as may be used to sense knee articulation indirectly. In this case, the data to be sensed and transmitted by the sensing part 110 may include pressure to the user's foot in motion, such as may occur when landing a jump.

In some embodiments, the sampling frequency of the sensing part 110 is adjustable. In another embodiment, the sampling frequency of the sensing part 110 is 50 Hz about 1,000 Hz. For example, the sampling frequency of the sensing part 110 may be 100 Hz or 500 Hz. The data for each of the motions sensed by the sensing part 110 may be transmitted in real time to the analyzing part 120 through a wire or in a wireless manner.

In some embodiments, a threshold differentiating knee joint articulations from other motions may be preset in the analyzing part 120. Once data received about a motion exceed the threshold, the analyzing part 120 transmits a trigger signal to the stimulating part 130. Otherwise, no trigger signal will be sent out of the analyzing part 120 if the received data do not exceed the threshold, and the analyzing part 120 will process subsequent data. The preset threshold preset in the analyzing part 120 may be adjustable for users with different weights or for different uses or activities such as in walking, sporting, climbing, or according to the various sport. For example, in a sport such as basketball which includes a significant level of jumping and knee bending movement may benefit from using a different threshold than running or walking.

In some embodiments, the threshold may be set so as to be indicative of any substantial knee joint articulations, such as may occur in any jumping or sprinting movement, or the threshold may be raised so as to be indicative of only knee joint articulations associated with significant jumps or forward drop landing movements. For example, jumping a distance of more than one foot off the ground or performing a drop landing task from a platform elevated by one foot or more would produce substantially more acceleration and impact than a normal walking movement. In such embodiments, the device may provide stimulation to select lower body muscles each time such knee articulation is determined (e.g. each time the user jumps regardless of the alignment of the joints, valgus displacement or internal rotation). This aspect is advantageous since it does not require differentiation between different types of knee joint articulation once the threshold is met. In addition, since the muscle stimulation provided by the device is controlled to correlate to proper muscle coordination, when the knee joint articulation occurs in a jump having the proper alignment, the stimulation to the muscles tends to occur when the muscles would normally contract such that the stimulation does not interfere with the coordination and alignment of the lower body in such cases. When the knee joint articulation has excessive valgus displacement or internal rotation having an increased likelihood of knee sprain, whether due to misalignment of the lower body or poor muscle coordination, the stimulation to the muscles occurs earlier than would normally occur such that the stimulation reduces the excessive valgus displacement or internal rotation, thereby preventing the knee sprain injury.

In other embodiments, the threshold may be set so as to be indicative of a particular type of knee joint articulation, such as a knee joint articulation having excessive knee valgus displacement, knee valgus velocity, internal rotation displacement or internal rotation velocity or any combination thereof. Such movements may be more likely to result in knee sprain injuries such that it may be useful to only stimulation or a user's position in combination with knee joint articulation. This aspect is advantageous as it reduces the possibility of interfering with other movements that may involve significant knee joint rotation and further allows the device to conserve energy, increasing the battery life of the device, since the electric stimulation is delivered only when needed, rather than with each significant knee joint articulation.

In certain other embodiments, the device may include a combination of the features described above, such as multiple threshold indicative of different types of knee joint articulations or knee joint articulations of differing magnitudes, such that the device may deliver differing types of muscle stimulation according to the different type or magnitude of knee joint articulation detected.

In another aspect, methods for preventing knee sprain using the device in accordance with an example device are described in further detail as follows. Once the device is applied to the patient, the sensing part is activated and begins sensing data relating to knee joint movement or articulation which is then transmitted to the analyzing part 120, which then determines whether the sensed data is indicative of a particular knee joint articulation, such as a knee sprain movement. Upon determination of such a movement, the analyzing part 120 sends a trigger signal to the stimulating part 130. Once the stimulating part 130 receives a trigger signal from the analyzing part 120, the controlling circuit 132 delivers an electric stimulation signal to electrodes 133 and 134 so as to generate a pulse current through select thigh and hip muscles, such as the gluteus medius and the biceps femoris, of the user. In some embodiments, the electric stimulation signal is an electric potential difference in pulse at a desired level.

When an electrical signal passes through the select thigh or hip muscle group, the muscles are stimulated earlier than they might otherwise be stimulated naturally, particularly in the case of misalignment of the lower body or poor muscle coordination. In such cases, the user is stimulated to reduce the excessive valgus displacement or internal rotation often so as to prevent the knee from an acute knee sprain injury. In particular, when a pulse current from the controlling circuit 132 is delivered through the electrodes 133 and 134 to one or both of the gluteus medius and the biceps femoris, the muscles contract earlier than would occur naturally thereby reducing or correcting the excessive valgus displacement or internal rotation of the knee joint during articulation, thereby preventing knee sprain injury associated therewith.

According to certain embodiments, the electrical signal from the controlling circuit 132 can be delivered through the muscle group within 20-30 ms after the start of a knee joint movement associated with sprain injury as determined by the analyzing part. A knee sprain injury typically occurs about 50 ms after start of the injurious movement. It is known that the torque latency of the muscles is about 21-25 ms. Therefore, with the stimulation provided by the device, the reaction time to a sprain injury is short enough such that the thigh and hip muscle can catch up to initiate muscle contraction to protect the knee joint.

In certain other embodiments, the electrical source 131 is a set of batteries. By using the electrical source 131, the controlling circuit 132 can output a pulse with a peak voltage of about 100-200 V. In some embodiments, the stimulation delivered is about 130 V through an electrode pair to a thigh or hip muscle, such either or both of the gluteus medius and biceps femoris. Although the peak voltage is relatively high, the current is small enough to ensure the safety for the user and still initiate early contraction of the muscle to prevent knee sprain injury.

The electrodes may be of various sizes and configuration so long as the electrodes are suitable to deliver myoelectric stimulation to the select muscles. In some embodiments, the device uses electrodes have an electrode surface area of between 10-50 square centimeters, or the device may include a combination of electrodes of differing size. In some embodiments, the electrodes 133 and 134 are separated by a distance of 1-3 cm on the skin surface of each of the select thigh and hip muscles. Optionally, the electrodes 133 and 134 are disposable/replaceable skin-attached silver chloride discs. Furthermore, the electrodes 133 and 134 can be embedded in any accompanying brace or athletic garment with a storage room lower body. There may be accompanying apparel which should not block the direct contact of the electrodes 133 and 134 and the skin surface.

For safety purposes and to conserve battery life, the control circuit of the device may be configured such that the device is de-activated or in a sleep mode when the design is not being worn and no skin impedance is detected by the electrodes 133 and 134. Moreover, the controlling circuit 132 may also include an on-off switch or adjustment to allow a user to selectively activate the device or adjust its operation according to the user's needs.

The physical variable to be sensed by the sensing part 110 and compared with the threshold may be any of variables characterizing motion of a knee joint during knee joint articulation. In some embodiments, the knee valgus displacement is the physical variable to be sensed. Then, the threshold differentiating sprain motions from normal motions is selected to be a bit higher than the range of the knee valgus displacement during normal knee joint motions so as to provide adequate protection. The range of the knee valgus displacement and internal rotations of the knee during normal movements can be obtained via trials.

In another aspect, the velocity of one or both of the knee valgus and internal rotation may be sensed directly or indirectly. This feature may be advantageous in some application since excessive velocity of knee valgus and internal rotation may indicate an impending sprain movement even before excessive knee valgus or internal rotation could indicate such movement. Thus, stimulation in response to exceeding a threshold of knee valgus or internal rotation velocity may deliver the muscle stimulation needed to prevent the impending sprain movement more effectively than a threshold based only one excessive knee valgus or internal rotation angles. In some embodiments, the threshold is approximately 30 to 1000 degrees per second. Optionally, the threshold may be adjustable according to the application or the requirements of the user. For example, the threshold can be set higher when the user is having a high intensity exercise such as running, hiking, playing basketball and the like.

In one aspect, the device may be incorporated, in whole or in part, into a wearable device such as a brace-like or the like, or more suitably, an athletic garment worn on the lower body such as a tight-fitting short or legging that helps adhere the electrodes of the stimulating part against the skin on the select thigh and hip muscles and supporting the one or more sensors of the sensing part in their respective locations on the user. Such a garment is particularly useful for recreational and professional athletes in all sports for preventing sport-related injury.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. Variations and modification made by those skilled in the art according to the disclosure herein should be within the scope of the present invention.

What is claimed is:

1. A device for preventing knee sprain injuries in a user, comprising:
    a sensing part configured to sense data associated with knee joint articulation, wherein the sensing part includes one or more sensors adapted to be positioned above the knee and one or more sensors adapted to be positioned below the knee when the device is worn by the user;
    an analyzing part in communication with the sensing part, the analyzing part having a processor configured to analyze the data to determine whether a detected knee joint articulation is a knee sprain motion associated with a knee sprain injury and to generate a trigger signal based on a determination of knee sprain motion; and a stimulating part in communication with the analyzing part, the stimulating part having a power supply and one or more electrode pairs configured to deliver a myoelectric stimulation in response to the trigger signal such that when the one or more electrode pairs are applied on one or more thigh or hip muscles associated with knee joint articulation, the myoelectric stimulation initiates an early muscle reaction of the one or more thigh or hip muscles to prevent the knee sprain injury.

2. The device of claim 1, wherein the sensed data corresponds to any of a knee valgus displacement, knee valgus velocity, an internal rotation displacement, an internal rotation velocity or any combination thereof.

3. The device of claim 2, wherein the determination of knee sprain motion comprises determining the detected knee joint articulation is a sprain motion when the knee joint articulation exceeds a preset threshold indicative of knee sprain injuries.

4. The device of claim 3, wherein the threshold is adjustable.

5. The device of claim 3, wherein the threshold is between approximately 30 and 1000 degrees per second.

6. The device of claim 1, wherein one or both of the one or more sensors adapted to be positioned above the knee and the one or more sensors adapted to be positioned below the knee include a batch of sensors that extend circumferentially at least partially around a thigh or shank of the user when the device is worn by the user.

7. The device of claim 6, wherein the analyzing part includes an algorithm to filter or average sensed data from the batch of sensor to remove errors associated with movement of a skin of the user on which the batch of sensor is supported.

8. The device of claim 1, wherein a data set associated with the knee joint articulation sensed by the sensing part is transmitted in real-time to the analyzing part in a wired or wireless manner and the sensing part has a sampling frequency in a range of 50 Hz to 1000 Hz.

9. The device of claim 1, wherein the sensing part is attached to a brace or apparel wearable such that when worn by a user during articulation of the knee, the sensing part senses the data associated with knee joint articulation.

10. The device of claim 1, wherein the sensing part comprises one or more sensors, the one or more sensors including a uniaxial or tri-axial accelerometer, gyrometer, goniometer, pressure sensor, a fabric strain sensor, or any combination thereof.

11. The device of claim 1, wherein the electrodes are adapted to be coupled to a skin surface of the one or more thigh and hip muscles, the one or more thigh and hip muscles being of a hip abductor/adductor group and/or a knee internal/external rotator group.

12. The device of claim 11, wherein the electrodes of each electrode pair are separated by a separation distance of between 1 cm to 5 cm when coupled to the skin surface of the thigh and hip muscles on the hip abductor/adductor group and/or the knee internal/external rotator group.

13. The device of claim 1, wherein the electrodes have an electrode contact surface area within a range of about 30 to 50 square centimeters.

14. The device of claim 1, wherein the myoelectric stimulation signal is an electrical pulse.

15. The device of claim 14, wherein the electrical pulse has a plurality of cycles with an adjustable width.

16. A device for preventing knee sprain injuries in a user, comprising:
a sensing part configured to sense data associated with knee joint articulation;
an analyzing part in communication with the sensing part, the analyzing part having a processor configured to analyze the data to determine whether a detected knee joint articulation is a knee sprain motion associated with a knee sprain injury and to generate a trigger signal based on a determination of knee sprain motion; and
a stimulating part in communication with the analyzing part, the stimulating part having a power supply and one or more electrode pairs configured to deliver a myoelectric stimulation in response to the trigger signal such that when the one or more electrode pairs are applied on one or more thigh or hip muscles associated with knee joint articulation, the myoelectric stimulation initiates an early muscle reaction of the one or more thigh or hip muscles to prevent the knee sprain injury,
wherein the device is incorporated, in whole or in part, into a brace, sock, legging, pair of shorts, pair of pants, or other supporting structure or wearable apparel such that when worn by a user, the stimulation part is coupled with one or more thigh or hip muscles of the user to deliver myoelectric stimulation thereto and the sensing part is positioned so as to detect the knee joint articulation of the user.

17. A method for preventing knee sprain injuries, said method comprising:
sensing data relating to a knee joint articulation;
analyzing the data to determine whether the sensed knee joint articulation is a sprain motion associated with knee sprain injuries;
generating a trigger signal based on a determination that the knee joint articulation is a sprain motion; and
stimulating one or more thigh and hip muscles in response to the trigger signal to initiate an early muscle reaction of the one or more thigh and hip muscles to prevent knee sprain injury.

18. The method of claim 17, wherein determining whether the sensed knee joint articulation is a sprain motion comprises determining that the indicated knee joint articulation is a sprain motion when the knee joint articulation exceeds a preset threshold associated with knee sprain injuries.

19. The method of claim 18, further comprising:
adjusting the threshold according to a characteristic of a user or according to an activity in which the user is engaged.

20. The method of claim 18, wherein the threshold is between approximately 30 and 1000 degrees per second.

21. The method of claim 17, wherein the sensed data relating to knee joint articulation corresponds to any of a knee valgus displacement, knee valgus velocity, an internal rotation displacement, an internal rotation velocity or any combination thereof.

22. The method of claim 17, wherein the sensed data relating to knee joint articulation is sensed in a real-time manner with a sampling frequency adjustable in a range of 50 Hz to 1000 Hz.

23. The method of claim 17, wherein sensing data comprises using one or more sensors, the one or more sensors including a uniaxial or tri-axial accelerometer, gyrometer, goniometer, pressure sensor, a fabric strain sensor, or any combination thereof.

24. The method of claim 17, wherein the one or more thigh and hip muscles comprise muscles of the hip abductor/adductor group and/or the knee internal/external rotator group, including the gluteus medius and biceps femoris, respectively.

25. The method of claim 17 wherein stimulating the one or more thigh and hip muscles with an electrical pulse.

26. The method of claim 25, wherein the electrical pulse has a plurality of cycles with an adjustable width.

27. The method of claim 17 further comprising:
sensing data relating to one or both of a foot motion or pressure;
analyzing the data to determine whether the sensed data corresponds to a forward drop landing movement;
generating a trigger signal based on a determination that the data corresponds to a drop landing movement regardless of whether the movement is a knee sprain motion; and
stimulating one or more thigh and hip muscles in response to the trigger signal according to a desired proper muscle coordination associated with the forward drop landing regardless of whether the movement is a knee sprain motion such that, when the forward drop landing movement is a knee sprain motion, the stimulating of the one or more thigh and hip muscles initiate an early muscle reaction of the one or more thigh and hip muscles than would otherwise occur so as to inhibit knee sprain injury.

* * * * *